United States Patent [19]

Kulpe et al.

[11] Patent Number: 5,543,564
[45] Date of Patent: Aug. 6, 1996

[54] PROCESS FOR RELEASING ACIDIC ORGANIC COMPOUNDS FROM SALTS THEREOF BY CARBON DIOXIDE

[75] Inventors: Jürgen Kulpe, Frankfurt; Heinz Strutz, Usingen; Hans-Martin Rüffer, Hofheim; Siegbert Rittner, Mörfelden-Walldorf, all of Germany

[73] Assignee: Hoechst Aktiengesellschaft, Frankfurt, Germany

[21] Appl. No.: 371,153

[22] Filed: Jan. 11, 1995

[30] Foreign Application Priority Data

Jan. 13, 1994 [DE] Germany ............... 44 00 751.5

[51] Int. Cl.$^6$ .............. C07C 63/36; C07C 27/34; C07C 29/74
[52] U.S. Cl. .............. 562/467; 562/8; 562/89; 562/431; 562/475; 562/477; 562/490; 562/485; 562/494; 562/580; 562/593; 562/600; 562/608; 568/716; 568/735; 568/749; 568/914; 568/918; 568/919
[58] Field of Search .............. 562/89, 431, 467, 562/475, 477, 490, 485, 494, 580, 593, 600, 608, 8; 568/716, 735, 749, 914, 918, 919

[56] References Cited

U.S. PATENT DOCUMENTS

| | | | |
|---|---|---|---|
| 3,655,744 | 4/1972 | Yasuhara | 260/521 R |
| 3,845,119 | 10/1974 | Duke et al. | 260/527 R |
| 4,180,681 | 12/1979 | Leonard et al. | 562/600 |
| 4,250,331 | 2/1981 | Shimshick | 562/485 |
| 4,282,323 | 8/1981 | Yates | 435/140 |
| 4,877,530 | 10/1989 | Moses | 210/511 |
| 5,175,354 | 12/1992 | Mitamura et al. | 562/481 |

FOREIGN PATENT DOCUMENTS

| | | |
|---|---|---|
| 0477928 | 4/1992 | European Pat. Off. . |
| 1155176 | 6/1969 | United Kingdom . |

OTHER PUBLICATIONS

Agnew Chem. Int. Ed. 30, No. 12, pp. 1643–1644. (1991).
Abstract JP-A-55/00322. (1980).
Abstract JP-A-50/01099. (1975).

*Primary Examiner*—Gary Geist
*Assistant Examiner*—Barbara S. Frazier
*Attorney, Agent, or Firm*—Curtis, Morris & Safford, P.C.

[57] ABSTRACT

This invention embodies a process for releasing acidic organic compounds in high yield and good purity from aqueous solutions of their salts which comprises converting the salts by carbon dioxide to their corresponding free acidic organic compounds and metal hydrogen carbonates, removing the acidic organic compounds from the mixture by extraction with an essentially water-insoluble organic solvent, and re-extracting the organic phase with carbon dioxide containing water. Using this process, the acidic organic compounds are completely released from their corresponding salts, i.e., the organic solution is free of salt. The acidic organic compounds released by the claimed process are organic compounds which contain acidic protons which can be replaced by metals. Some examples are carboxylic acids, sulfonic acids, phosphonic acids, phenols, naphthols, and aliphatic alcohols.

15 Claims, No Drawings

PROCESS FOR RELEASING ACIDIC ORGANIC COMPOUNDS FROM SALTS THEREOF BY CARBON DIOXIDE

The invention relates to a process for releasing acidic organic compounds from aqueous solutions of their salts by carbon dioxide in the presence of an essentially water-insoluble organic solvent.

Acidic organic compounds such as carboxylic, sulfonic or phosphonic acids are of importance in all areas of organic chemistry. For example, aromatic carboxylic acids and also aromatic hydroxyl compounds are starting compounds for a multiplicity of industrial applications such as the production of polyesters or polyamides. Polyesters can also be produced from hydroxycarboxylic acids by self-condensation. Aromatic sulfonic acids are versatile intermediates which are used, e.g., in dye and pigment production.

The preparation of aromatic hydroxyl compounds, carboxylic acids and sulfonic acids belongs to the prior art. This frequently passes through an alkaline reaction phase which makes a neutralization or acidification step necessary to release the products. The same applies to aromatic hydroxycarboxylic acids which are generally prepared by the so-called Kolbe-Schmitt reaction, starting from the hydroxyl compounds. In this case, the alkali metal salt of the corresponding hydroxyl compound is brought to reaction with carbon dioxide at elevated temperature, thus forming the alkali metal salt of the corresponding hydroxycarboxylic acid. This can be released and isolated by addition of a mineral acid. In this case, per gram atom of hydroxycarboxylic acid, two gram atoms of the alkali metal salt of the mineral acid used are formed. The alkali metal salts of the mineral acids cannot be used again for other reactions and thus represent an unavoidable production of salt which must be disposed of.

It is desirable to avoid this ecologically and economically unfavorable unavoidable production of salt in the release of the aromatic acidic compounds from their metal salts.

In a number of processes, instead of mineral acids, carbon dioxide is used as the gaseous acid anhydride of carbonic acid to release organic acids. The advantage of this procedure is the fact that the carbonic acid, in contrast to mineral acids, can easily be released again from its metal salts, the metal base being able to be recovered as valuable material. This is sometimes already achieved by increasing the temperature with formation of the metal oxides.

In the use of carbon dioxide as anhydride of carbonic acid in acid-base reactions, the existence of an apparent dissociation constant ($pK_s$) is problematic. This apparent dissociation constant characterizes the diminished acid strength of an aqueous carbonic acid solution. The apparent dissociation constant is composed of the actual first stage dissociation constant of carbonic acid and the preceding hydration equilibrium of physically dissolved carbon dioxide to give carbonic acid. This apparent dissociation constant has the effect that an acid which, according to a comparison of its dissociation constant with the first dissociation constant of carbonic acid, should be able to be released, is not actually able to be released. In practice, the comparison must be made with the apparent dissociation constant, as a result of which only a small number of acidic organic compounds can be completely released from their salts by carbonic acid. In the case of nonequilibrium reactions, it has been described (Ang. Chem. 103 (1991), 1689), that the establishment of the hydration equilibrium can be accelerated by increasing the pressure. Complete conversions are possible if the product formed as an acid by the action of carbon dioxide reacts and is thus removed from the equilibrium.

In the reaction of carbonic acid with alkali metal salts of organic acids, alkali metal hydrogen carbonates are formed which buffer the pH in aqueous solution and thus limit the the minimum pH achievable. This is bypassed in JP-A 50/01099 by adding a water-miscible organic solvent to the solution so that the solubility of the hydrogen carbonate formed is reduced. As a result the hydrogen carbonate precipitates out and is thus removed from the equilibrium. It is a disadvantage that the separation of the potassium hydrogen carbonate only succeeds to approximately 80%. The isolation of organic acids from their salts by means of carbon dioxide by addition of a water-immiscible hydrocarbon is described in JP-A 55/00322. It is a disadvantage of this process that the organic acid must be sufficiently soluble in the hydrocarbon, which is only the case in exceptions.

In U.S. Pat. No. 4,282,323, the removal and concentration of low-molecular organic acids from aqueous fermentation solutions by acidification with carbon dioxide and extraction of the acid with a polar organic solvent such as t-butanol are described.

Disadvantages of the process are the low yield and the contamination of the resulting acid with salts. This process is therefore in principle only suitable for those acids which can be simply separated off and purified by distillation.

It has now surprisingly been found that acidic organic compounds can be obtained in high purity and good yield if the polar organic solvent used for the extraction of the free acid from the aqueous phase is re-extracted with water under carbon dioxide pressure.

The invention relates to a process for releasing acidic organic compounds from aqueous solutions of their salts by carbon dioxide in the presence of an essentially water-insoluble organic solvent, which comprises re-extracting the organic phase with carbon dioxide-containing water.

In the process according to the invention, the acidic compounds are completely released from the corresponding salts, i.e. the organic solution is free of salts.

The products can be isolated from the organic solution by the conventional methods, e.g. evaporation or crystallization. The metal salts of carbonic acid retained in the aqueous phase may be either returned directly to the process as starting base or after evaporation, drying and, if appropriate, calcining, or else may be utilized in other versatile ways. It is of particular ecological and economic importance that the solvents used can be completely circulated.

Acidic organic compounds in the context of the invention are all organic compounds which contain acidic protons which can be replaced by metals. Examples are carboxylic acids, sulfonic acids, phosphonic acids, but also phenols, naphthols and aliphatic alcohols.

Acidic organic compounds are preferred which have a $pK_s$ of 2 to 10, particularly preferably 3 to 6. Carboxylic, hydroxycarboxylic and amino acids are very particularly preferably released from their salts by the process according to the invention, in particular 6-hydroxy-2-naphthalenecarboxylic acid, 3-hydroxy-2-naphthalenecarboxylic acid, salicylic acid, parahydroxybenzoic acid and Ph—$SO_2$—N($CH_3$)—($CH_2$)$_5$—COOH.

The starting compounds used in the process according to the invention are generally metal salts of the corresponding acidic organic compounds. Alkali metal salts and alkaline earth metal salts are preferably used, particularly preferably lithium salts, sodium salts and potassium salts, very particularly preferably sodium salts and potassium salts.

The salts of acidic organic compounds suitable for use in the process according to the invention can also be present in a small amount in a mixture with a large amount of other salts. Such salt mixtures arise, e.g., in Kolbe-Schmitt reactions and related reactions, as are described, for example, in GB-A 1 155 176 and U.S. Pat. No. 3,655,744.

The preparation of 6-hydroxy-2-naphthalenecarboxylic acid, termed HNA hereafter, may be mentioned by way of example. In the preparation of HNA, a reaction mixture arises which, in addition to the dipotassium salt of HNA, comprises 3-hydroxy-2-naphthalenecarboxylic acid (BONS), the dipotassium salt of BONS, potassium 2-naphtholate, the potassium salt of 6-hydroxy-2,7-naphthalenedicarboxylic acid (HNDA), potassium carbonate and potassium formate.

Fermentation solutions as are described, e.g. in U.S. Pat. No. 4,282,323 are equally suitable.

The metal salts used are converted by carbon dioxide to the corresponding free acidic organic compounds and metal hydrogen carbonates. The procedure is generally carried out under carbon dioxide pressure, preferably at pressures of 1 to 70 bar, particularly preferably 1 to 20 bar, very particularly preferably 2 to 6 bar.

The carbon dioxide can be fed, for example, via a stationary gas-introduction device, a hollow-shaft gas-introduction agitator, via the liquid surface or by presaturation of one or both liquid phases.

The acidic organic compound released in the acidification by carbon dioxide is removed from the reaction equilibrium by extraction with an essentially water-insoluble organic solvent.

Essentially water-insoluble, in the context of the invention, is taken to mean that two phases separated by a phase boundary form under the chosen extraction conditions.

Polar organic solvents are suitable such as alcohols, ketones, esters and ethers. Preferred solvents are 1-butanol, higher alcohols, secondary and tertiary alcohols. In the case of HNA, 1-butanol has proved to be a particularly expedient extraction medium.

The extraction can be performed continuously or discontinuously. All apparatuses which can maintain the required conditions for the extraction are suitable for the process according to the invention. Continuous and multistage liquid-liquid extractors in counter-current mode are preferred, e.g. mixer settlers, centrifugal extractors and column extractors according to the prior art (see, e.g., Ullmann's Encylopaedia of Industrial Chemistry, Vol. B3, 1988).

The process according to the invention is generally carried out at temperatures between the solid point of the solution and 150° C., preferably from −10° to 100° C., particularly preferably from 10° to 60° C.

According to the invention, the organic phase obtained in the above extraction is re-extracted with carbon dioxide-containing water.

During this, a carbon dioxide pressure is generally employed, preferably from 1 to 70 bar, particularly preferably from 1 to 20 bar, very particularly preferably from 2 to 6 bar. The re-extraction is generally carried out at a temperature between the solid point of the solution and 150° C., preferably from −10° to 100° C., particularly preferably from 10° to 60° C.

It can be performed continuously or discontinuously. For continuous re-extraction, for example, mixer settlers or extraction columns operated in counter-current mode are suitable.

All vessels which are suitable for operation under the said temperature and pressure conditions can be used to carry out the process according to the invention.

A possible way for carrying out the process according to the invention is described below for 6,2 HNA as an example:

The essentially water-insoluble organic solvent is first added to the salt or salt mixture (in the case of HNA: HNA dipotassium salt, 3-hydroxy-2-naphthalenecarboxylic acid dipotassium salt, potassium 2-naphtholate, HNDA tripotassium salt, potassium carbonate and potassium formate) occurring in the aqueous state or dissolved in water and the phases are mixed intimately by stirring. The mixture is then acidified by carbon dioxide under pressure until the pH is constant. The pH can be measured, for example, with a commercial pressure-resistant glass electrode.

After a stable pH is achieved, the organic phase is separated off, preferably under pressure, and the extraction is repeated, in the case of discontinuous work-up, if target compound is still contained in the aqueous phase. The aqueous phase can contain the organic solvent (in the case of HNA, preferably 1-butanol) in saturation concentration. This can be recovered by distillation, frequently utilizing azeotropes. The salt solution then remaining can be reused in the synthesis. If appropriate, in the case of discontinuous operation, the organic extracts are combined. In the case of HNA, in addition to 1-butanol, they contain water, potassium formate, potassium hydrogen carbonate in traces, free naphthol and HNA and BONS having 1 to 1.5 potassiums per molecule.

The solution is re-extracted with aqueous carbonic acid. In this case, the mixture is advantageously vigorously stirred or another suitable measure is taken in order to mix the two phases together intimately. When the pH no longer changes, organic and aqueous phases are separated. The procedure is repeated, if appropriate in the case of discontinuous operation, until the salt content of the organic phase has achieved the desired values.

The water phase arising in this extraction can contain small amounts of the organic solvent, and additionally, the metal content from the organic phase in the form of the hydrogen carbonate. However, some of the acidic organic compounds released are also coextracted into the water phase. In order not to lose this portion, the water phase can be conducted to the start of the process, used to dissolve the salt mixture and thus recirculated.

If the salts of different acidic organic compounds having differing $pK_sS$ are present in the aqueous solution, after the process according to the invention, the separation of these compounds by selective release of a compound can take place. These can be separated off, for example, by precipitation or extraction, extraction being preferred. Then, by further feed, the more strongly acidic compound can be released from its salt and can be isolated. In the case of HNA, it is possible, for example, first to selectively separate off β-naphthol which is present as K β-naphtholate and then to separate off HNA itself.

In addition, in the case of HNA, 6-hydroxy- 2,7-naphthalenedicarboxylic acid (HNDA) formed as a minor component in the preparation can be successfully separated off by filtration after the HNA extraction by choosing the extraction conditions in such a way that only less than 1% of the HNDA is extracted.

The free acidic organic compounds prepared according to the invention are generally so pure that they can be further reacted or used without further purification steps. If higher purities are desired, these can be achieved by recrystallization, in the case of HNA again from butanol. In particular, HNA prepared according to the invention can be reacted to form a polyester which is distributed, for example, under the name Vectra® by the Hoechst Celanese Corporation, USA. The invention will be described in more detail by the examples, without restricting it thereto.

In the examples, the reaction vessel is composed of an autoclave which has an internal volume of 2 liters and is temperature-controlled via a jacket. The autoclave is furnished with a pump for liquid metering, interior thermometer, pressure-resistant pH electrode, descender pipe and hollow-shaft gas-introduction agitator which is fitted with an agitator disk at half of its overall length. The stirrer is magnetically coupled to the drive. For pH measurement, a pressure-resistant electrode of the Ingold Company, Frankfurt, Infit® 764-50 type is used. pH measurements are taken with manual temperature compensation.

The content of organic compounds and of carbonate and formate ions was determined by high-pressure liquid chromatography (HPLC), and the potassium content was determined by AAS-spectroscopy. In the case of solids, the water content was determined by Karl-Fischer. It was not possible to differentiate between carbonate ions and hydrogen carbonate ions. The limits of detection for formate and carbonate ions were 0.01% (m/m).

EXAMPLES

1. Release of 6-hydroxy-2-naphthalenecarboxylic acid (HNA) from its dipotassium salt A solution composed of 17.8 g of HNA, 12.77 g of potassium hydroxide, 13.1 g of potassium carbonate, 237 g of potassium formate and 350 ml of water is heated in an autoclave to 50° C. 500 ml of 1-butanol are added to the aqueous solution and the two-phase system is vigorously stirred. A carbon dioxide pressure of 5 bar is then established in the gas space of the reactor. After one hour, the stirring is turned off, whereupon two liquid phases form. 470 ml of water-containing butanol phase are separated off via the descender pipe and after the reactor has been drained and rinsed, are pumped back into this. 670 ml of water are then pumped in. After 30 minutes, the stirring is interrupted, the organic and aqueous phases are separated and the organic phase is pumped back into the reactor. The re-extraction is repeated with 660 ml of water. After phase separation, 365 ml of butanol phase are isolated. The solvent is evaporated in vacuo and the residue obtained is dried overnight at 50° C. in a vacuum of < 20 mbar. 9.26 g of HNA are isolated as a pure white powder. Water content: 0.024%; melting point: 247° to 248° C.; the product contains no carbonate and formate in amounts detectable by HPLC analysis.

| calculated: | C 70.21 | H 4.28 | K 0 |
|---|---|---|---|
| found: | C 70.0 | N 4.15 | K 0.048 |

2. Release of 3-hydroxy-2-naphthalenecarboxylic acid (BONS) from its disodium salt The aqueous solution of a Kolbe-Schmitt reaction, as arises in the preparation of BONS, is used. The solution contains sodium 2-naphtholate, sodium carbonate, sodium hydroxide, 6-hydroxy-2-naphthalenecarboxylic acid and 3-hydroxy-2-naphthoic acid disodium salt. The solution has a pH of 13.35. 800 ml (≏837 g) of the solution are charged into the reactor and heated to 50° C. By careful addition of carbon dioxide, the pH is then decreased in the course of 10 minutes to a pH of 9. 7.5 g of a solid composed of 2-naphthol and resins precipitate out in the course of this and are separated off by filtration. After addition of 500 ml of 1-butanol, a carbon dioxide pressure of 5.45 bar is established in the gas phase. After 75 minutes, the stirring is stopped and the phases are separated. The organic phase is then re-extracted three times, each time with 220 ml of water, at 25° C. and 5.5 bar carbon dioxide pressure. From the butanol phase are isolated, as described in Example 1, 13.7 g of a brownish-yellow powder which is composed of a mixture of BONS, 2-naphthol and <1% of HNA. The sodium content of the product mixture is <1%.

Example 3: Separation of 2-naphthol by selective acidification in the presence of a suitable solvent Solution analogous to Example 2, but the reaction is carried out at 42° C. Before acidification, 150 ml of methyl tertiary-butyl ether are added. The pH is decreased to 7.75. The product is isolated by evaporating off the solvent in vacuo and drying the isolated solid at 40° C. at a pressure of 20 mbar overnight. 6.4 g of a brownish powder are isolated which is composed of 7.3% HNA, 0.2% BONS and 91.8% 2-naphthol. Based on the starting material, 94.8% of the 2-naphthol is isolated.

Comparison experiment: Separation by pH-selective precipitation of 2-naphthol without organic solvent A solution of 25.7 g of 84.2% pure potassium hydroxide, 6.2 g of naphthol, 35.3 g of 6,2-HNA, 2.7 g of BONS, 16.7 g of potassium carbonate and 45 g of potassium formate in 640 ml of water is heated in the reactor to 50° C. By means of carbon dioxide addition, the pH is decreased to 8.0. A light-brown solid precipitates out in the solution. The solid is filtered off by suction, washed with water and dried. 4.75 g of a light-brown powder were isolated which is composed of 2.2% HNA, 0.9% BONS and 93% 2-naphthol. This is 71% of theory, based on 2-naphthol isolated.

Example 4: Release of 1-naphthalenecarboxylic acid from its potassium salt 500 ml of 1-butanol were added to an alkaline solution composed of 20 g of 1-naphthalenecarboxylic acid and 10 g of potassium hydroxide in 500 ml of water in a 2 liter stainless steel autoclave and the mixture was stirred vigorously at room temperature with a constant pressure blanketing with carbon dioxide of 5.0 bar. The autoclave is provided with a self-inducing hollow-shaft agitator for gas distribution into the emulsion. After one hour the agitator is switched off and the two phases are given the opportunity to separate. The two phases are taken off separately, still under pressure, with the aid of a descender pipe, 488 g of light phase and 411 g of heavy phase being obtained. All of the light phase together with 1000 ml of water is subjected to a single re-extraction as described in Example 1. In this case, 355 g of light phase are isolated which contain, after distilling off the solvent, 18.72 g of the product in dry form having a potassium content below 0.4%.

Found: Yield: 94% Acidification: 99%

Example 5: Release of benzoic acid from its potassium salt

An alkaline solution composed of 20 g of benzoic acid and 20 g of potassium hydroxide in 500 ml of water was treated in the same manner as in Example 4. The light phase of 366 g obtained after a single re-extraction contains, after distilling off the solvent, 23.32 g of the product in dry form having a potassium content of 1.2%.

Found: Yield: 29% Acidification: 96%

Example 6: Release of 1-naphthalenesulfonic acid from its potassium salt

An alkaline solution composed of 40 g of 1-naphthalenesulfonic acid and 40 g of potassium hydroxide in 500 ml of water is treated in the same manner as in Example 4. The light phase of 366 g obtained after single re-extraction contains, after distilling off the solvent, 2.32 g of the product in dry form having a potassium content of 7.9%.

Found: Yield: 5% Acidification: 55%

Example 7: Release of

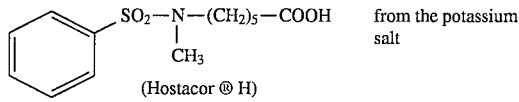 from the potassium salt (Hostacor ® H)

20 g of Hostacor® are made alkaline and dissolved in 500 ml of demineralized water with 12.5 g of potassium hydroxide solution (50%). The solution is then vigorously stirred with 500 ml of butanol for 1 h under 4 bar of $CO_2$ in a 2 l autoclave equipped with a high-speed hollow stirrer. After separation of the phases, the butanol phase is then re-extracted three times with 500 ml of demineralized water under the same conditions. The remaining butanol phase (360 g) is concentrated by evaporation and the residue is dried in a drying cabinet.

Yield: 70% Acidification: 95% (Potassium content= 0.04%)

Example 8: Re-use of the re-extraction water to dissolve the salt mixture

A) A solution of 25.7 g of potassium hydroxide (84.2% pure), 6.2 g of 2-naphthol, 2.8 g of 3-hydroxy-2-naphthoic acid, 35.3 g of 6-hydroxy-2-naphthoic acid, 16.7 g of potassium carbonate and 45 g of potassium formate in 670 ml of water is heated in the autoclave to 50° C. and carbon dioxide is gradually added to it until the solution has a pH of 8. The solution is filtered via a pressure filter. 4.35 g of a light-brown solid are isolated which is composed of more than 89% of 2-naphthol (63% of theory) and of 2.3% of HNA (0.3% of theory). The filtrate is returned to the autoclave, 400 ml of aqueous butanol are added, the mixture is blanketed at 24° C. with 5.3 bar carbon dioxide pressure and vigorously stirred. When the pH ceases to change, the stirring is stopped and the organic phase is separated off. The extraction is then repeated three times, each time with 250 ml of aqueous butanol. The organic phases are combined and re-extracted four times, each time with 200 ml of water under 5.3 bar carbon dioxide pressure. 1053 g of butanol phase are then isolated. The solvent is evaporated off in vacuo and the resulting residue is dried overnight at 50° C. in a vacuum of <20 mbar. 31.7 g of a light-brown powder are isolated which is composed of 88.2% HNA (79% of theory), 7.2% BONS (81% of theory) and 5.3% 2-naphthol (27% of theory). The potassium content is below 0.8%.

The heavier water-rich phases isolated in the re-extraction are combined. The butanol is removed by distillation of the azeotrope, 700 ml of water phase being obtained.

B) Example 8 A is repeated, the 700 ml of back-extraction water which was obtained and freed from butanol in Example 8 A being used to dissolve the potassium hydroxide, naphthol, 3-hydroxy-2-naphthoic acid, 6-hydroxy-2-naphthoic acid, potassium carbonate and potassium formate. 36.9 g of a light brown powder are isolated by work-up of the re-extracted butanol phase. The powder is composed of 88.5% of HNA, this corresponds to 92.5% of the amount of HNA used in the experiment, and is additionally composed of 6.45% of BONS (85% of theory) and 5.1% of naphthol (30% of theory).

Example 9: Separation of 6-hydroxy-2,7-naphthalenedicarboxylic acid

If, in addition to the amount described in Example 8 A, 5.4 g of 6-hydroxy-2,7-naphthalenedicarboxylic acid (HNDA) and 5.9 g of potassium hydroxide are dissolved and the procedure is then followed as described further, only 1.1% of the amount of HNDA used is found in the residue of the butanol phase. More than 80% of the amount of HNDA used can be isolated by filtration of the salt solution remaining after the butanol extraction. About 3% of the amount of HNDA used remains in the solution itself.

We claim:
1. A process for releasing an acidic organic compound from an aqueous solution of its salt which comprises:
    a) converting the salt by carbon dioxide to its corresponding free acidic organic compound and metal hydrogen carbonate;
    b) removing the acidic organic compound from the reaction mixture by extraction with an essentially water-insoluble organic solvent; and
    c) re-extracting the organic phase obtained in said extraction with carbon dioxide containing water.
2. The process according to claim 1 wherein the conversion of the salt and/or the extraction and/or the re-extraction are carried out under carbon dioxide pressure.
3. The process according to claim 2 wherein the carbon dioxide pressure is between 1 and 70 bar.
4. The process according to claim 3 wherein the carbon dioxide pressure is between 1 and 20 bar.
5. The process according to claim 1 wherein the extraction and the re-extraction are carried out at a temperature between the solidifying point of the aqueous solution and 150° C.
6. The process according to claim 1 wherein the temperature is from −10° to 100° C.
7. The process according to claim 1 wherein the organic solvent is selected from the group consisting of alcohols, esters, ketones, and ethers.
8. The process according to claim 7 wherein the organic solvent is selected from the group consisting of 1-butanol, higher alcohols, secondary alcohols, and tertiary alcohols.
9. The process according to claim 1 which is carried out continuously.
10. The process according to claim 1 wherein the salt of the acidic organic compound is an alkali metal salt or an alkaline earth metal salt.
11. The process according to claim 10 wherein the salt of the acidic organic compound is selected from the group consisting of lithium salts, sodium salts, and potassium salts.
12. The process, according to claim 1 wherein acidic organic compounds having differing $pk_s$ are present in the solution, which comprises
    converting the salt of a lesser acidic organic compound by carbon dioxide to its corresponding free acidic organic compound and metal hydrogen carbonate,
    removing the acidic organic compound from the reaction mixture by extraction with an essentially water-insoluble organic solvent, and
    re-extracting the organic phase obtained in said extraction with carbon dioxide containing water;
    then, by further feed of carbon dioxide, converting the salt of a more strongly acidic organic compound to its corresponding free acidic organic compound and metal hydrogen carbonate,
    removing the acidic organic compound from the reaction mixture by extraction with an essentially water-insoluble organic solvent, and re-extracting the organic phase obtained in said extraction with carbon dioxide containing water such that a selective separation of the acidic organic compounds is achieved.

13. The process according to claim 1 wherein the acidic organic compound is selected from the group consisting of carboxylic acids, sulfonic acids, phosphoric acids, phenols, naphthols, and aliphatic alcohols.

14. The process according to claim 1 wherein the acidic organic compound has a $pk_s$ value of 2 to 1.

15. The process according to claim 1 wherein the acidic organic compound is 6-hydroxy-2-naphthalene carboxylic acid.

* * * * *